US012599740B2

(12) United States Patent
    Veis

(10) Patent No.: US 12,599,740 B2
(45) Date of Patent:   Apr. 14, 2026

(54) ORAL APPLIANCE FOR USE WITH CPAP HEADGEAR

(71) Applicant: R.I.P., LLC, Chatsworth, CA (US)

(72) Inventor: Rob Veis, Malibu, CA (US)

(73) Assignee: R.I.P., LLC, Chatsworth, CA (US)

( * ) Notice: Subject to any disclaimer, the term of this patent is extended or adjusted under 35 U.S.C. 154(b) by 717 days.

(21) Appl. No.: 17/909,722

(22) PCT Filed: Mar. 8, 2021

(86) PCT No.: PCT/US2021/021406

§ 371 (c)(1),
(2) Date: Sep. 6, 2022

(87) PCT Pub. No.: WO2021/178972

PCT Pub. Date: Sep. 10, 2021

(65) Prior Publication Data

US 2024/0207558 A1      Jun. 27, 2024

Related U.S. Application Data

(60) Provisional application No. 62/986,558, filed on Mar. 6, 2020.

(51) Int. Cl.
    *A61M 16/06*       (2006.01)
    *A61F 5/56*        (2006.01)

(52) U.S. Cl.
    CPC ........... *A61M 16/0683* (2013.01); *A61F 5/56* (2013.01); *A61M 16/0666* (2013.01); *A61M 2210/0637* (2013.01); *A61M 2210/0643* (2013.01)

(58) Field of Classification Search
    CPC .......... A61C 7/08; A61F 5/0006; A61F 5/566; A61M 2210/0637
    See application file for complete search history.

(56) References Cited

U.S. PATENT DOCUMENTS

| 2,705,006 A | * | 3/1955 | Cettel | ..................... A61F 5/566 |
| | | | | 128/857 |
| 3,178,820 A | * | 4/1965 | Kesling | .................... A61C 7/08 |
| | | | | 128/861 |
| 3,898,736 A | * | 8/1975 | Bergersen | ................ A61C 7/08 |
| | | | | 433/6 |
| 5,624,257 A | * | 4/1997 | Farrell | ..................... A61C 7/08 |
| | | | | 128/861 |

(Continued)

OTHER PUBLICATIONS

Search Report and Written Opinion issued in corresponding International Patent Application No. PCT/US2021/021406 dated Jun. 17, 2021.

*Primary Examiner* — Valerie L Woodward
(74) *Attorney, Agent, or Firm* — LOZA & LOZA, LLP; Michael Fedrick

(57)          ABSTRACT

An oral appliance for use by a subject while wearing a nasal CPAP mask having an occlusal opening between a buccal portion and a lingual portion of a dental tray which allows centric occlusion. The upper and lower receptacle portions of the tray have interproximal protrusions to provide intimate contact between the appliance and a user's teeth to assist in retaining the user's jaws in place and prevent them from opening. The appliance includes buccal wall which extends into the vestibule of the user's mouth to assist in creating an intraoral seal.

14 Claims, 13 Drawing Sheets

(56)        References Cited

U.S. PATENT DOCUMENTS

| | | | | |
|---|---|---|---|---|
| 5,645,420 | A | * | 7/1997 | Bergersen ................ A61C 7/08 |
| | | | | 433/6 |
| 5,752,510 | A | * | 5/1998 | Goldstein ......... A61M 16/0666 |
| | | | | 128/207.14 |
| 5,983,892 | A | | 11/1999 | Thornton |
| 2017/0216084 | A1 | | 8/2017 | Veis |
| 2019/0274871 | A1 | | 9/2019 | Veis et al. |
| 2020/0015937 | A1 | * | 1/2020 | Stewart .................. B32B 27/36 |

* cited by examiner (Prior Art)

(Prior Art)

(Prior Art)

ORAL APPLIANCE FOR USE WITH CPAP HEADGEAR

CROSS-REFERENCE TO RELATED APPLICATIONS

This application is the U.S. national stage of International Patent Application No. PCT/US2021/021406 filed on Mar. 8, 2021, which claims the benefit of priority under 35 U.S.C. § 119 (e) from U.S. Patent Application No. 62/986,558 filed on Mar. 6, 2020. The disclosures of the foregoing applications are incorporated herein by reference in their entirety.

BACKGROUND

Sleep apnea is a disorder characterized by abnormal pauses in breathing or instances of abnormally low breathing during sleep. Each pause in breathing, called an apnea, can last from a few seconds to minutes (typically lasting 20 to 40 seconds) and may occur 5 to 30 times or more an hour. Sleep apnea results from a partial-to-complete blockage of a subject's airway. Increased air speed through the airway causes an increase in dynamic pressure and a corresponding drop in static pressure. The decreased static pressure can in some instances draw back the lower jaw and tongue and thereby block the airway. This blockage can increase to the point of becoming complete, which at least temporarily interrupts breathing.

One treatment for sleep apnea involves the use of a Continuous Positive Airway Pressure ("CPAP") system, in which an air flow generator pushes air through a mask into the patient's airway to keep it open during sleep. The masks used in CPAP systems can cover either the nose and mouth or just the nose of a user. Masks covering both the nose and mouth are referred to as full-face masks, while masks covering only the nose are referred to as nasal masks.

While CPAP therapy provides considerable benefit, including improved breathing and oxygenation, noncompliance by patients is a major concern for medical professionals and insurance carriers. Persistent problems arising with CPAP therapy include air leakage, pain, discomfort, and a constricted airway. When the mouth partially opens during treatment with a nasal mask, CPAP treatment can become ineffective due to leakage of air through the mouth. Gastric insufflation (air in the stomach) may also result as the airway becomes constricted. As a consequence of these and other problems, some patients avoid CPAP therapy or use it only sporadically.

SUMMARY

The present oral appliance is for use by a subject while wearing a nasal CPAP mask in order to treat apnea in the subject. The appliance 10 comprises a dental tray 100 having a lingual side 111, a buccal side 113, an anterior portion 112, a posterior portion 114, a right side 116, a left side 118, an inner surface 117, an outer surface 119, an upper side 122, and a lower side 124. The dental tray is generally bounded by a buccal wall 131, a lingual wall 133, an upper receptacle portion 230, and a lower receptacle portion 231.

The buccal wall 131 has an outer surface on the buccal side 113 of the dental tray and includes a right buccal side 135 which extends from the anterior portion 112 of the tray to the posterior portion 114 on the right side 116 and a left buccal side 138 which extends from the anterior portion 112 of the tray to the posterior portion 114 on the left side 118. The buccal wall 131 can include an upper frenum notch 512 in the anterior portion of the buccal wall 131 in order to accommodate the frenum of a user of the appliance 10, and can also include a lower frenum notch 514. The upper end of the buccal wall 131 can extend beyond the gingival margin of a predetermined tooth by about 4-6 mm, and/or can extend ⅔ of the distance between the gingival margin and the top of the vestibule. On the lower end, of the buccal wall 131 can likewise extend beyond the gingival margin of a predetermined tooth by about 4-6 mm, and/or can extend ⅔ of the distance between the gingival margin and the top of the vestibule. The upper and lower edges of the buccal wall 131 in some embodiments can extend to at least the alveolar mucosa of the user.

The lingual wall 133 has an outer surface on the lingual side 111 of the dental tray and includes a right lingual side 132 which extends from the anterior portion 112 of the tray to the posterior portion 114 on the right side 116 and a left lingual side 134 which extends from the anterior portion 112 of the tray to the posterior portion 114 on the left side 118. The lingual wall 133 can likewise include an upper frenum notch and/or a lower frenum notch.

Joining portions 127 in the posterior portion of the tray connect the buccal wall 131 and lingual wall 133. A right side joining portion 126 is attached on a proximal end to the posterior portion 114 of the lingual wall 133 on the right side 116, and the distal end is attached to the posterior portion 114 of the buccal wall 131 on the right side 116. A left side posterior joining portion 128 is attached on a proximal end to the posterior portion 114 of the lingual wall 133 on the left side 118 while the distal end is attached to the posterior portion 114 of the buccal wall 131 on the left side 118. When the appliance tray 100 is formed from a thermoplastic material, the joining portions 127 can be integrally formed with the appliance tray 100. Alternatively, the joining portions can be formed from a metal wire, which can be embedded in the material forming the buccal wall 131 and lingual wall 133, respectively.

The dental tray 100 further includes an occlusal opening 125 extending between the buccal wall 131 and the lingual wall 133 from the anterior portion of the tray to the posterior portion of the tray. In some embodiments the occlusal opening 125 forms an open channel which extends continuously between the buccal wall 131 and the lingual wall 133 from the anterior portion of the tray to the posterior portion of the tray. This allows a user's teeth to contact each other so that the user can close the mouth normally.

The dental tray 100 also includes an upper receptacle portion 230 on the inner surface 137 of the upper side 122 of the tray and a lower receptacle portion 231 on the inner surface 137 of the lower side 124 of the tray. The upper receptacle portion 230 includes a plurality of maxillary dentition recesses 502 for receiving maxillary dentition of the subject, and the lower receptacle portion 231 includes a plurality of mandibular dentition recesses 504 for receiving mandibular dentition of the subject. The receptacles both include interproximal protrusions 505 which extend inwardly from the inner surface 137 of the upper and lower receptacle portions. Each interproximal protrusion 505 is located between adjacent dentition recesses in the receptacles in order to engage interproximal spaces between the subject's teeth when the appliance is worn.

In use, contact between the inner surface 137 and interproximal protrusions 505 of the dental tray 100 facilitates maintenance of the subject's jaws in a closed position, thereby allowing the buccal wall 131 to contact the subject's lips and form an intraoral seal. The present appliance can thus be included in a system for treating apnea which includes the appliance and a nasal CPAP mask. The appliance and system are used to treat apnea by applying the appliance to the subject, i.e. so that the subject is wearing the oral appliance, and then applying a nasal CPAP mask.

FIGURES

Figure 1:
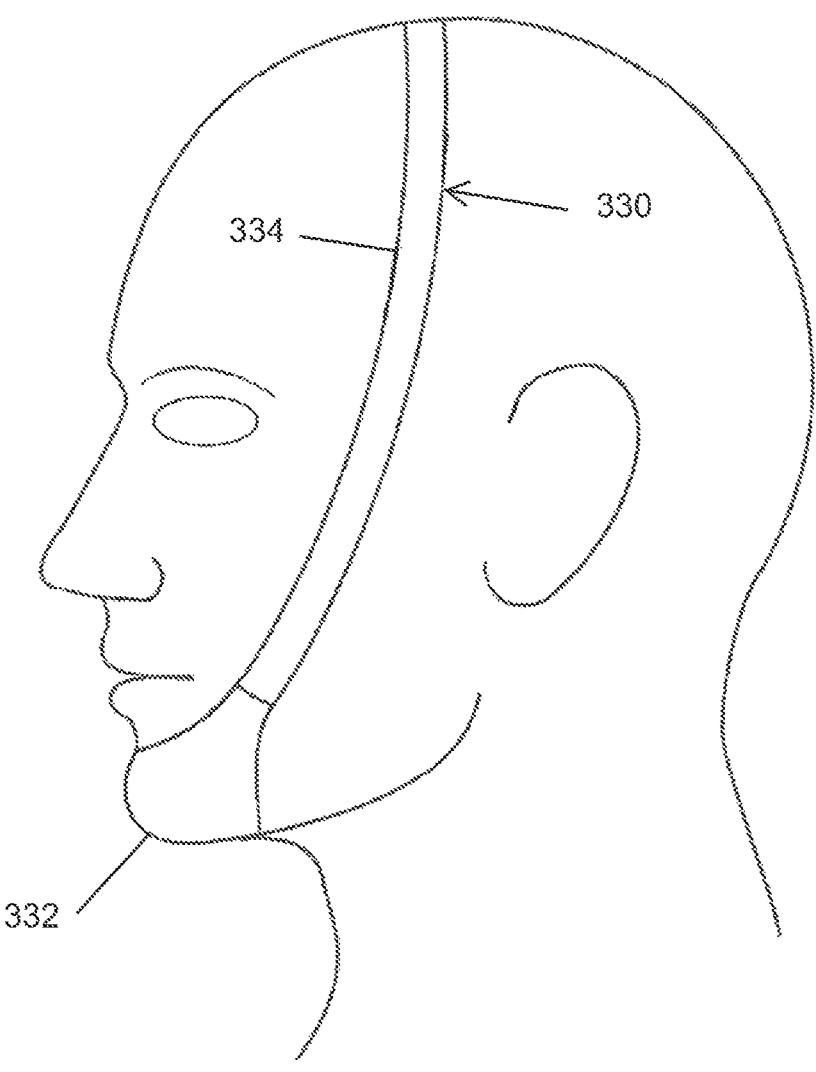
FIG. 1 is a left side elevation view of a subject wearing a chinstrap for use with a CPAP mask and headgear.

The reference numbers in the figures have the following meanings:

| Component | Subcomponent | Reference Number |
|---|---|---|
| subject | | 1 |
| | maxillary dentition | 2 |
| | mandibular dentition | 3 |
| | gingival margin | 4 |
| | lips | 5 |
| oral appliance | | 10 |
| | buccal portion | 12 |
| | lingual portion | 14 |
| dental tray | | 100 |
| | lingual side | 111 |
| | buccal side | 113 |
| | anterior portion | 112 |
| | posterior portion | 114 |
| | right side | 116 |
| | left side | 118 |
| | inner surface | 117 |
| | outer surface | 119 |
| | upper side | 122 |
| | lower side | 124 |
| | occlusal opening | 125 |
| | joining portion | 127 |
| | right side posterior joining portion | 126 |
| | left side posterior joining portion | 128 |
| | buccal wall | 131 |
| | lingual wall | 133 |
| | right lingual side | 132 |
| | left lingual side | 134 |
| | right buccal side | 136 |
| | left buccal side | 138 |
| receptacle | | 130 |
| | inner surface | 137 |

4

-continued

| Component | Subcomponent | Reference Number |
|---|---|---|
| | upper receptacle portion | 230 |
| | lower receptacle portion | 231 |
| headgear | | 310 |
| | sagittal strap | 315 |
| | lateral strap | 320 |
| | upper lateral strap | 321 |
| | right side end | 322 |
| | left side end | 324 |
| | lower lateral strap | 325 |
| | right side end | 326 |
| | left side end | 328 |
| | chinstrap | 330 |
| | chin retaining portion | 332 |
| | strap portion | 334 |
| nasal mask | | 350 |
| | anterior portion | 352 |
| | posterior portion | 354 |
| | right side | 356 |
| | left side | 358 |
| | outer surface | 359 |
| | upper end | 362 |
| | lower end | 364 |
| posterior wire | | 400 |
| | left side posterior wire | 410 |
| | proximal end | 412 |
| | distal end | 414 |
| | right side posterior wire | 420 |
| | proximal end | 422 |
| | distal end | 424 |
| tray recess | | 500 |
| | maxillary dentition recess | 502 |
| | mandibular dentition recess | 504 |
| | interproximal protrusion | 505 |
| frenum notch | | 510 |
| | upper frenum notch | 512 |
| | lower frenum notch | 514 |
| tooth model | | 515 |
| occlusal plane | | 520 |

DESCRIPTION

Definitions

As used herein, the following terms and variations thereof have the meanings given below, unless a different meaning is clearly intended by the context in which such term is used. Terms relating to location and orientation (e.g., "downward," "horizontal," "anterior," etc.) are intended to be relative, but for convenience are generally described below with reference to the placement or orientation of the appliance or a component thereof when the appliance is worn by a subject.

"About" and "approximately" refer to a quantity or distance within 10% of the referenced quantity or distance, unless the circumstances of such usage would indicate a different meaning.

"Anterior" means in the direction of or toward or adjacent the front portion (opening) of a subject's mouth when the present appliance is in use by a subject.

"Apnea" and "sleep apnea" refer to a temporary cessation of breathing and/or to instances of shallow or infrequent breathing during sleep, generally caused by a blockage of a subject's airway (referred to as obstructive sleep apnea).

"Arcuate" refers to a surface or shape which is curved, i.e. in the manner of a bow.

"Axial plane" refers to an imaginary plane that divides the body into cranial and caudal (upper and lower) portions.

"Buccal" means in the direction of or toward a subject's cheek. In relation to a subject's teeth, this refers to the side of the teeth facing the cheek.

"Coronal" refers to a position or direction which is on or toward the distal end of a tooth (i.e., where the biting surface is located). A "coronal surface" is thus the biting surface of a tooth, which can alternatively be referred to as an "occlusal surface."

"Dental tray" refers to a structure comprising a receptacle for receiving the teeth of a subject.

"Downward" and "downwardly" mean in the direction of or toward a lower portion of a subject's body. "Upward" and "upwardly" mean in the opposite direction, i.e. in the direction of or toward an upper portion of a subject's body.

"Elongated" refers to a configuration or shape having a length which is longer than its width.

"Frenum" refers to a piece of tissue of a subject which is attached to and connects a portion of the subject's gum either to the lip or the tongue. An upper labial frenum attaches the maxillary gum to the upper lip, while a lower labial frenum attaches the mandibular gum to the lower lip.

"Horizontal," with respect to the present appliance, refers to disposition in a plane approximately parallel to the axial plane of a subject and/or to a plane on which the coronal surfaces of a subject's teeth meet when the subject closes the mouth. With respect to a component of the present appliance, "horizontal" refers to such disposition when the appliance is in use by a subject.

"Interproximal," with respect to the present appliance, refers to an area between teeth. Interproximal space refers to the space between two adjacent teeth in either the maxillary or mandibular dentition.

"Labial" means in the direction of, toward, or adjacent to a subject's lips. In relation to a subject's teeth or a portion of the present appliance adjacent a subject's teeth during use of the appliance, this refers to the side facing the lips.

"Lateral" means away from the sagittal plane of a subject or from the center of the present appliance.

"Left" means to the left of the center sagittal plane of a subject, from the perspective of the subject, or to the left of the present appliance when it is worn by a subject.

"Lingual" means in the direction of, toward, or adjacent to a subject's tongue. In relation to a subject's teeth or a portion of the present appliance adjacent a subject's teeth during use of the appliance, this refers to the side facing the tongue.

"Lower" refers to the relative position of a component in the present appliance which is closer to or toward a lower portion of a subject's body when the appliance is being used.

"Mandibular" refers to the lower jaw.

"Mandibular dentition" refers to the teeth of the lower jaw.

"Maxillary" refers to the upper jaw.

"Maxillary dentition" refers to the teeth of the upper jaw.

"Medial" means toward the sagittal plane of a subject or toward the center of the present appliance.

"Notch" refers to a portion of a component of the present appliance which has a height or width which is less than an adjacent portion of that component.

"Occlusal plane" refers to a hypothetical plane formed by the occlusal surfaces of the teeth when the jaw is closed. An occlusal plane can be determined by a person of skill in the art and may take into account deviations with respect to certain teeth of a subject.

"Posterior," "rear," and "rearward" mean in the direction of or toward or adjacent the rear portion of a subject's mouth, i.e. the back of the mouth (away from the front teeth), or to a component of the present appliance which is located in this way when worn by a subject.

"Receptacle" refers to a portion of the present appliance having a space of sufficient size and volume to receive and retain a portion of a user's dentition in the receptacle.

"Right" means to the right of the center sagittal plane of a subject, from the perspective of the subject, or to the right of the present appliance when it is worn by a subject.

"Sagittal plane" refers to an imaginary plane that travels vertically from the top to the bottom of the body of a subject, dividing it into left and right portions.

"Subject" refers to a user of the present appliance.

"Thermoplastic" refers to a material, generally a polymer material, which may be softened by heat and hardened by cooling in a reversible physical process. The thermoplastic materials used in some components of the present appliance retain their shape at 100° F. and preferably become soft (deformable) at a temperature of 212° F. or below.

"Tray" and "dental tray," as used herein, refer to a generally U-shaped portion of the present appliance comprising open areas for receiving the maxillary or mandibular teeth of a subject, as the case may be.

"Upper" refers to the relative position of a component in the present appliance which is closer to or toward an upper portion of a subject's body when the appliance is being used.

"Vertical," with respect to the present appliance, refers to a disposition toward or away from a subject's head or feet, which can be approximately parallel to a horizontal plane as defined herein.

"Vestibule" refers to the part of the mouth bounded anteriorly and laterally by the lips and the cheeks, posteriorly and medially by the teeth and gums, and in the upper jaw includes the area of hard tissue above the teeth to where the inner cheek attaches to maxilla.

"Wear" with respect to an oral appliance as described herein refers to the placement of the appliance into the mouth of a user and then closing the user's mouth so that the appliance is in contact with the user's teeth. With respect to a CPAP nasal mask, wearing such a mask refers to placement of the mask over the user's nose in order to deliver pressurized air to the user.

The term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise. Ranges which are described as being "between" two values include the indicated values.

CPAP Appliance

The present oral appliance 10 is adapted to retain a user's mouth and jaw in a closed position while at the same time facilitating the sealing of the user's mouth to the appliance to prevent the leakage of air from the CPAP system through the mouth. The appliance 10 generally retains the user's upper and lower dentition in a relaxed, closed position, i.e. in the manner that the user would naturally close his or her mouth with their normal bite. At the same time, the inner (labial) portion of a user's lips rests on a buccal wall of the appliance during use, thereby providing a seal that prevents the flow of air through the user's mouth. Providing such a seal allows air to be directed by a nasal CPAP system into a user's airway at a relatively reduced pressure.

The appliance 10 comprises a dental tray 100 which has an anterior portion 112, a posterior portion 114, a right side 116, a left side 118, a lingual side 111, a buccal side 113, an inner surface 117, an outer surface 119, an upper side 122, and a lower side 124. The tray 100 is generally U-shaped so as to be able to fit over a user's maxillary and mandibular dentition. The tray 100 can be formed from a variety of orally compatible materials, though thermoplastic polymers are preferred.

The present appliance 10 includes an occlusal opening 125 which extends between the upper side 122 and lower side 124 of the tray 100, and extends substantially between the anterior portion 112 and posterior portion 114 of the appliance. In a preferred embodiment, the occlusal opening 125 extends continuously from the posterior portion 114 on the right side 116 of the appliance to the posterior portion 114 on the left side 118 of the appliance, forming an open channel between a buccal portion 12 and a lingual portion 14 of the appliance 10. The open channel allows the occlusal surfaces of a user's maxillary dentition and mandibular dentition to come into contact while the appliance 10 is worn by a user, so that the teeth are positioned in a manner which is the same as or similar to the normal bite of the user while not wearing the present appliance 10. By allowing such occlusal contact, a user's mouth will be fully closed while wearing the present appliance, allowing the user's lips to stay closed more easily during sleep. By contrast, most prior art appliances comprise two trays or receptacles for a user's maxillary and mandibular dentition and have a layer of material in between such dentition, and thus do not allow a user's teeth to come together, thereby forcing the jaws into a more open position and making it difficult for the user's lips to remain closed, especially during sleep.

The occlusal opening 125 is also advantageous for manufacturing the present appliance when they are formed as individualized appliances for a particular user's dentition. Models or impressions of a subject's teeth are made for use in making such individualized appliances, and to form the present appliance the modeled teeth can simply be arranged in accordance with the subject's natural mouth closure (bite). When a layer of material is included between a subject's mandibular and maxillary dentition, as with prior appliances, the placement of such modeled teeth is frequently not centric, i.e. the mandible and maxilla are not positioned in the way that user would do so naturally, which results in discomfort. This problem is avoided with the present appliance.

In one embodiment, the present appliance does not cause any mandibular repositioning or change in occlusion, but instead allows centric (normal) occlusion, i.e. a normal bite while the appliance is worn. This provides comfort to the user of the present appliance and assists in forming a seal between the appliance 10 and the user's mouth, as described further below. In other embodiments, the position of the recesses in the lower receptacle portion 231 for the mandibular dentition can be advanced toward the anterior portion of the mouth with respect to the position of the recesses in the upper receptacle portion 230 for the maxillary dentition, in the manner of other apnea appliances. This positioning brings a user's tongue forward and assists in maintaining the user's airway open during sleep, and so may reduce the amount of pressure needed to be introduced by a CPAP device in order to maintain the user's airway open and thereby treat or avoid apnea.

In some embodiments, the user's maxillary and/or mandibular dentition may contact the inner surface 137 of the upper receptacle portion 230 and/or the lower receptacle portion 231 may contact the user's dentition and such contact between some occlusal surfaces.

The dental tray 100 further comprises a buccal wall 131 on the outer surface of the buccal portion 12, i.e. the surface facing the lips and cheek of a user while the appliance 10 is being worn, and the lingual portion 14 comprises a lingual wall 133 facing the tongue. The buccal wall 131 preferably comprises a continuous, smooth outer surface, both for user comfort and to assist in forming an intraoral seal, and the lingual wall 133 likewise preferably comprises a continuous, smooth outer surface. In order to assist both in keeping a user's mouth in a closed position and forming an intraoral seal during use, the buccal wall 131 preferably extends upwardly with respect to the user's occlusal plane 520 (see FIG. 10) beyond the gingival margin 4 (or gum line, where a tooth becomes exposed) and over the gingiva or gums, i.e. the tissue of the upper and lower jaws that surrounds the base of the teeth, and into the vestibule of the user's mouth. The buccal wall 131 can extend upwardly to the top of the vestibule (i.e., to the mucogingival junction), where the inner cheek attaches to maxilla, and preferably extends at least ⅔ of the distance between the gingival margin and the top of the vestibule, in order to better assure that an intraoral seal is formed between a user's lips and the appliance 10 during use. Preferably, the buccal wall 131 extends upwardly above a user's gingival margin 4 (for a predetermined tooth) by about 4-6 mm (millimeters) to the upper side 122 of the dental tray 100, for example be extending about 4, 4.5, 5, 5.5, or 6 millimeters above a user's gingival margin 4. Alternatively, the buccal wall 131 can be measured as extending upwardly from the occlusal plane 520 by between 11 and 18 millimeters, such as by about 11, 12, 13, 14, 15, 16, 17, or 18 mm.

The buccal wall 131 can also extend downwardly from the occlusal plane 520 below a user's gum line, such as by about 4-6 mm beyond the user's gingival margin for a predetermined tooth and/or by at least ⅔ of the distance between the gingival margin and the bottom of the vestibule. For example the buccal wall 131 can extend downwardly about 4, 4.5, 5, 5.5, or 6 millimeters below a user's gingival margin 4. Alternatively, the buccal wall 131 can be measured as extending downwardly from the occlusal plane 520 by between 11 and 18 millimeters, such as by about 11, 12, 13, 14, 15, 16, 17, or 18 mm. In one embodiment, the buccal wall 131 extends above and/or below the user's mucogingival junction to or beyond the alveolar mucosa of a user. The lingual wall 133 can extend above and below a user's occlusal plane 520 by the same distance as the buccal wall 131, but in some embodiments can be shorter, i.e., the upper and lower edges of the lingual wall 133 can extend by a shorter distance from the occlusal plane 520 as compared to the buccal wall 131, since this portion of the appliance doesn't directly participate in forming an intraoral seal.

In embodiments in which the buccal wall 131 extends beyond the frenum tissue in the maxilla and/or mandible, a frenum notch 510 can be provided in the anterior portion 112 of the buccal wall 131. An upper frenum notch 512 for the maxillary frenum can have a vertical extent or length above the user's occlusal surface which is less than the extent (height) of the buccal wall 131 on the right side and left side of the upper frenum notch 512. Likewise, a lower frenum notch 514 can have a vertical extent or length below the user's occlusal surface which is less than the downward extent of the buccal wall 131 on the right side and left side of the lower frenum notch 514.

Figure 4:
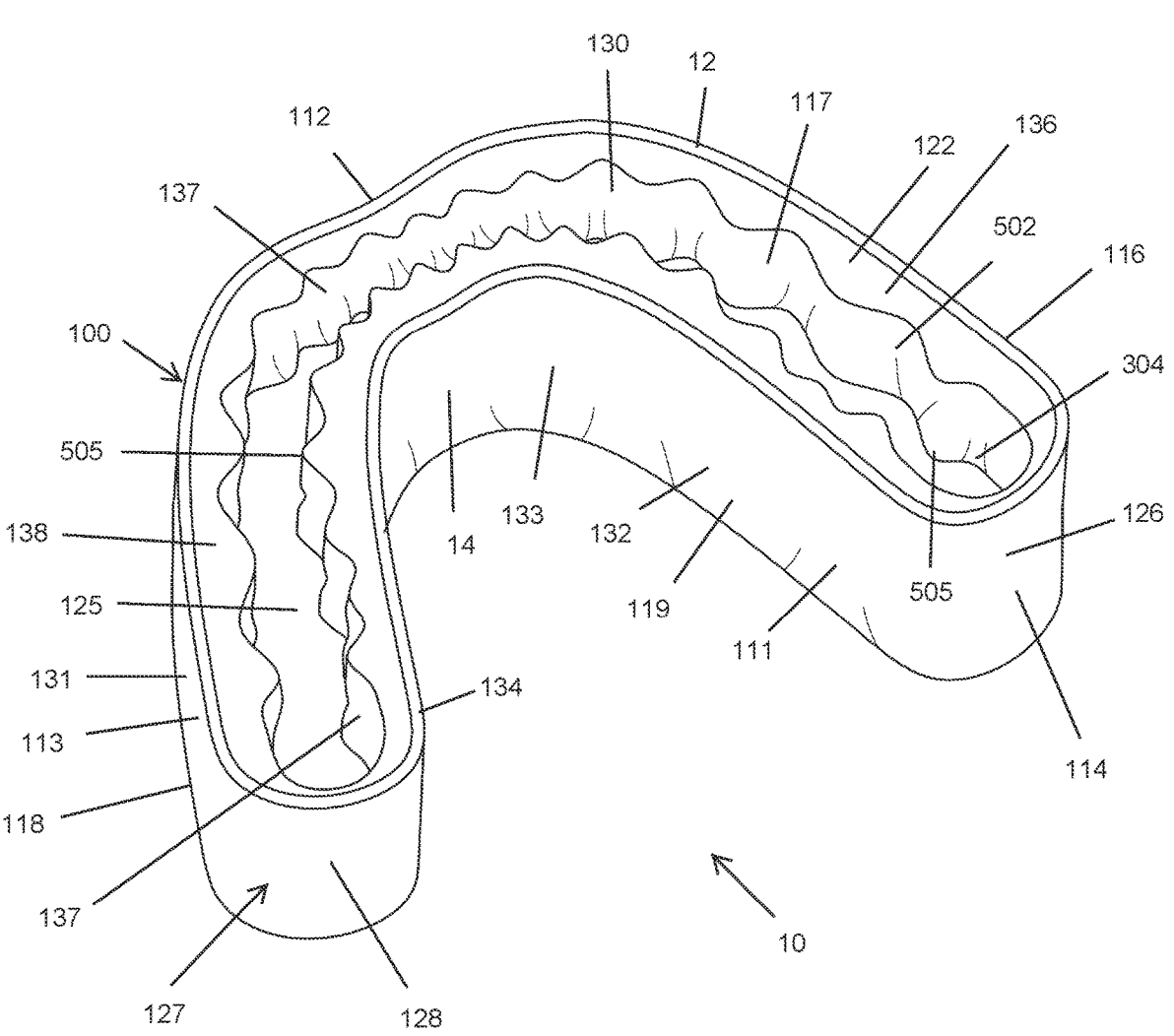
FIG. 4 is a top perspective view of a first embodiment of the present oral appliance.
Figure 5:
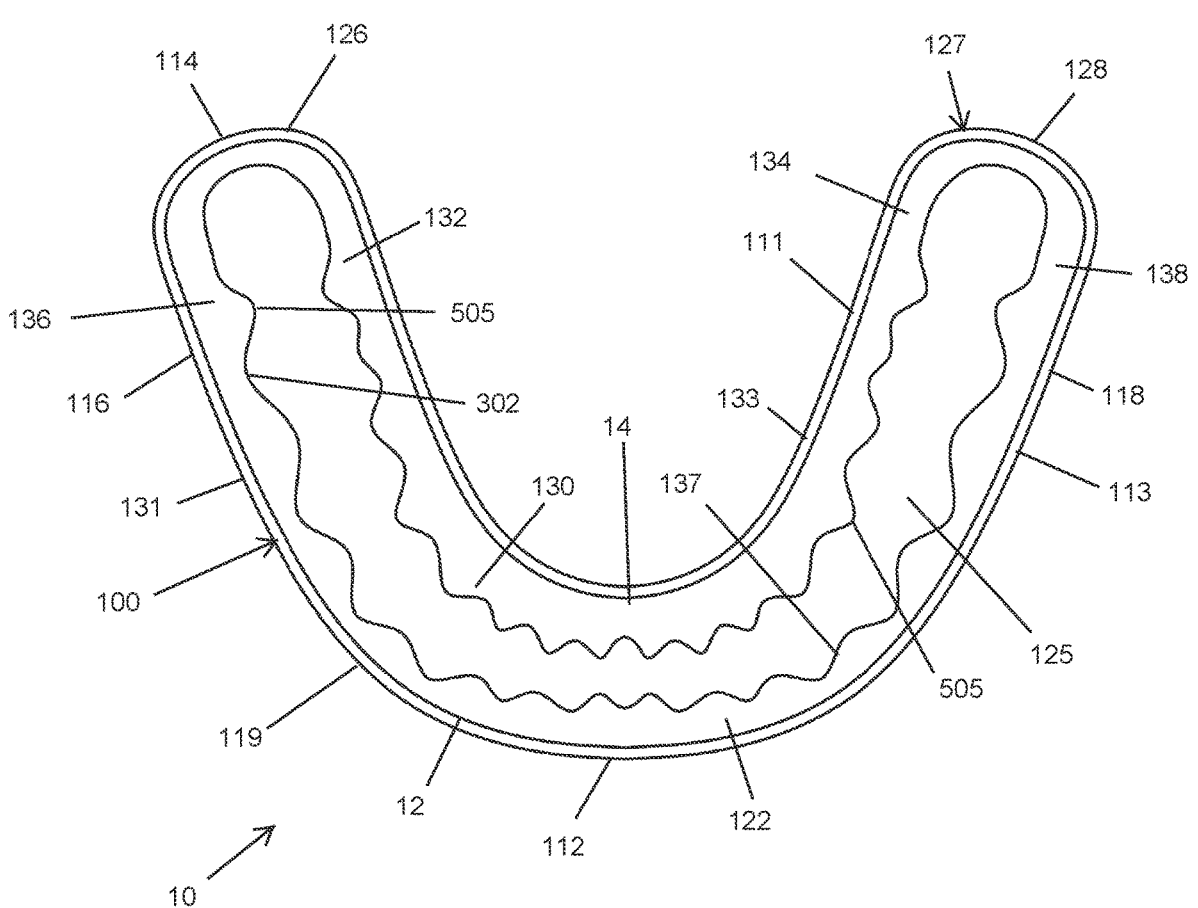
FIG. 5 is a top plan view of the oral appliance of FIG. 4.
Figure 6:
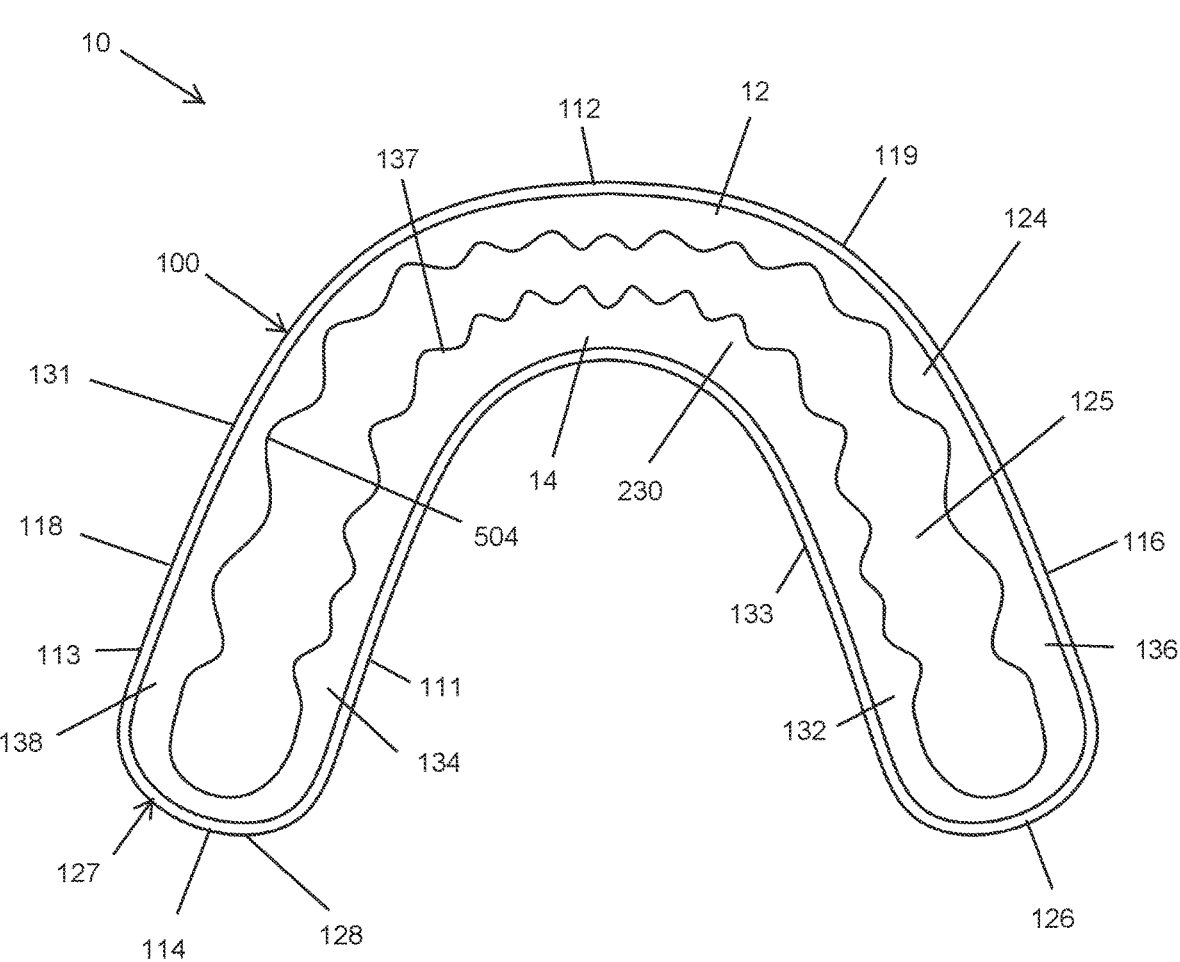
FIG. 6 is a bottom plan view of the oral appliance of FIG. 4.
Figure 7:
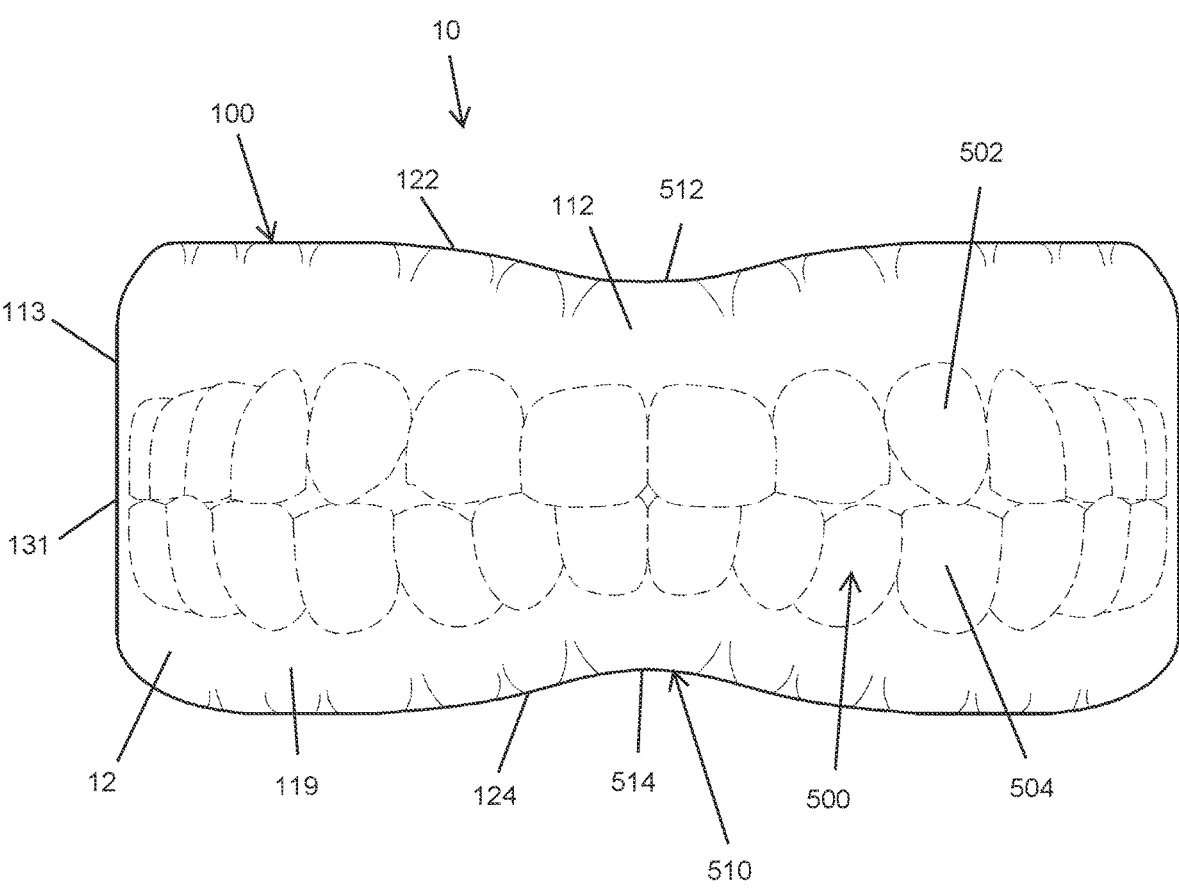
FIG. 7 is a front elevation view of the oral appliance of FIG. 4.
Figure 8:
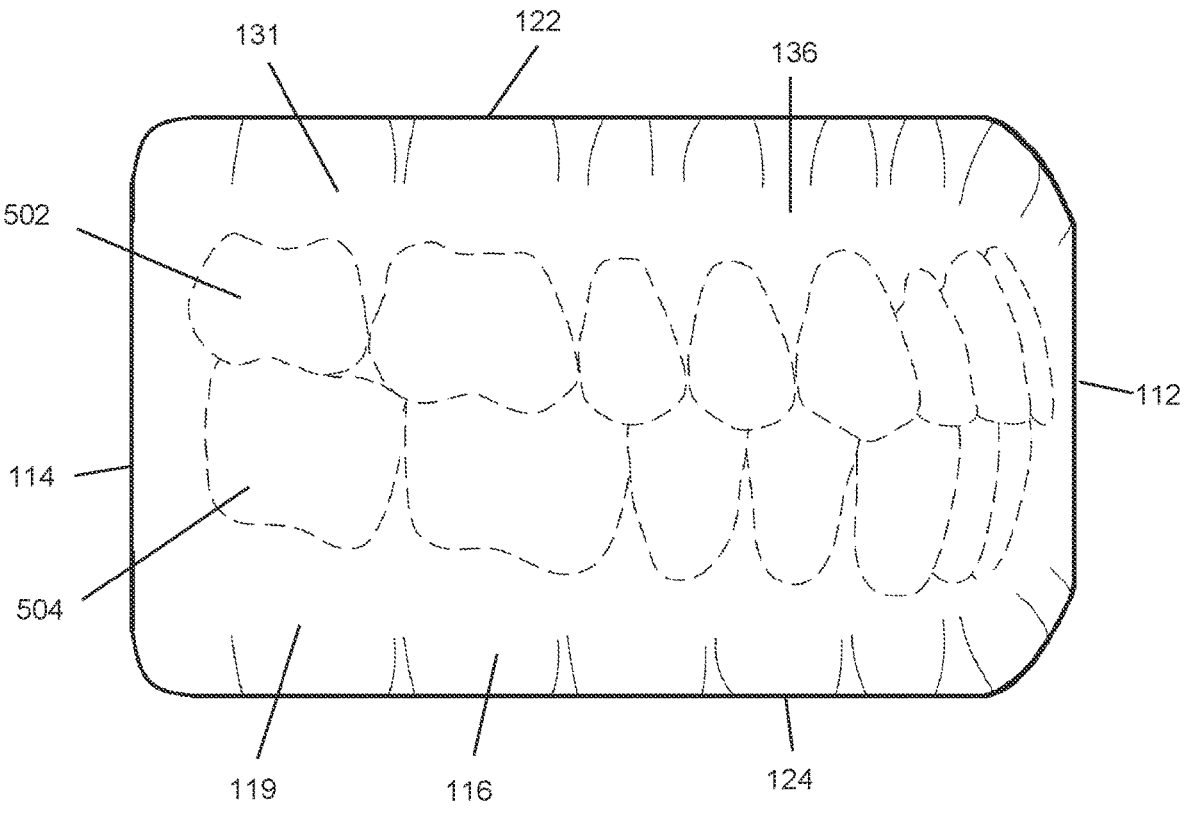
FIG. 8 is a right side view of the oral appliance of FIG. 4.
Figure 9:
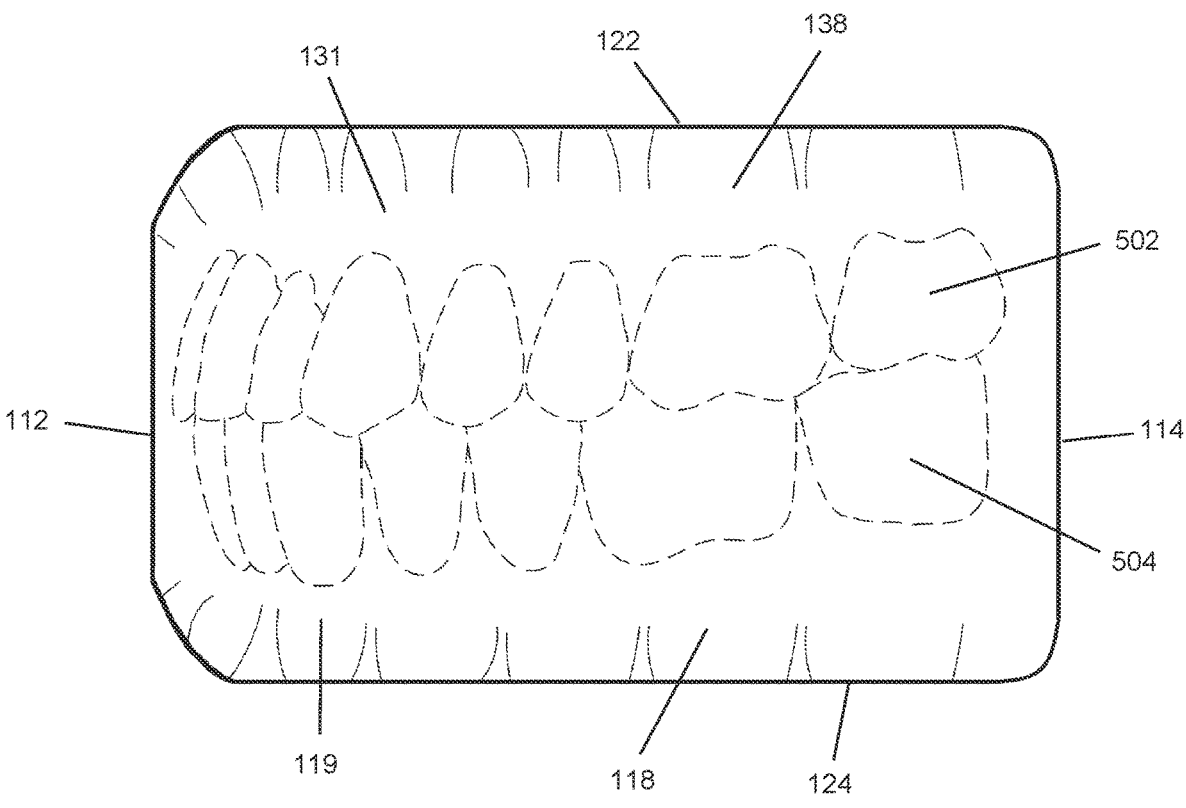
FIG. 9 is a left side view of the oral appliance of FIG. 4.
Figure 11:
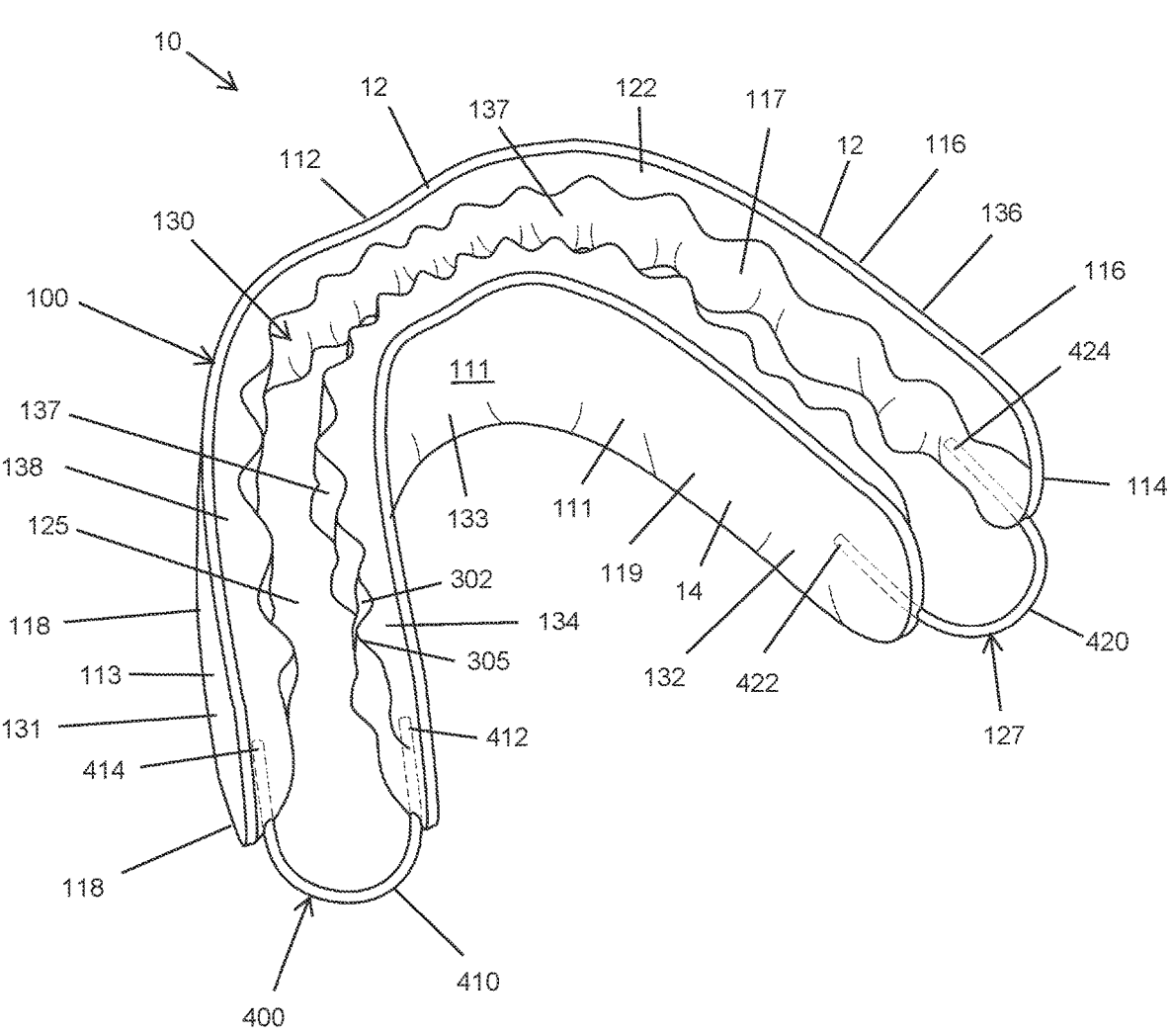
FIG. 11 is a top perspective view of a second embodiment of the present oral appliance.
Figure 12:
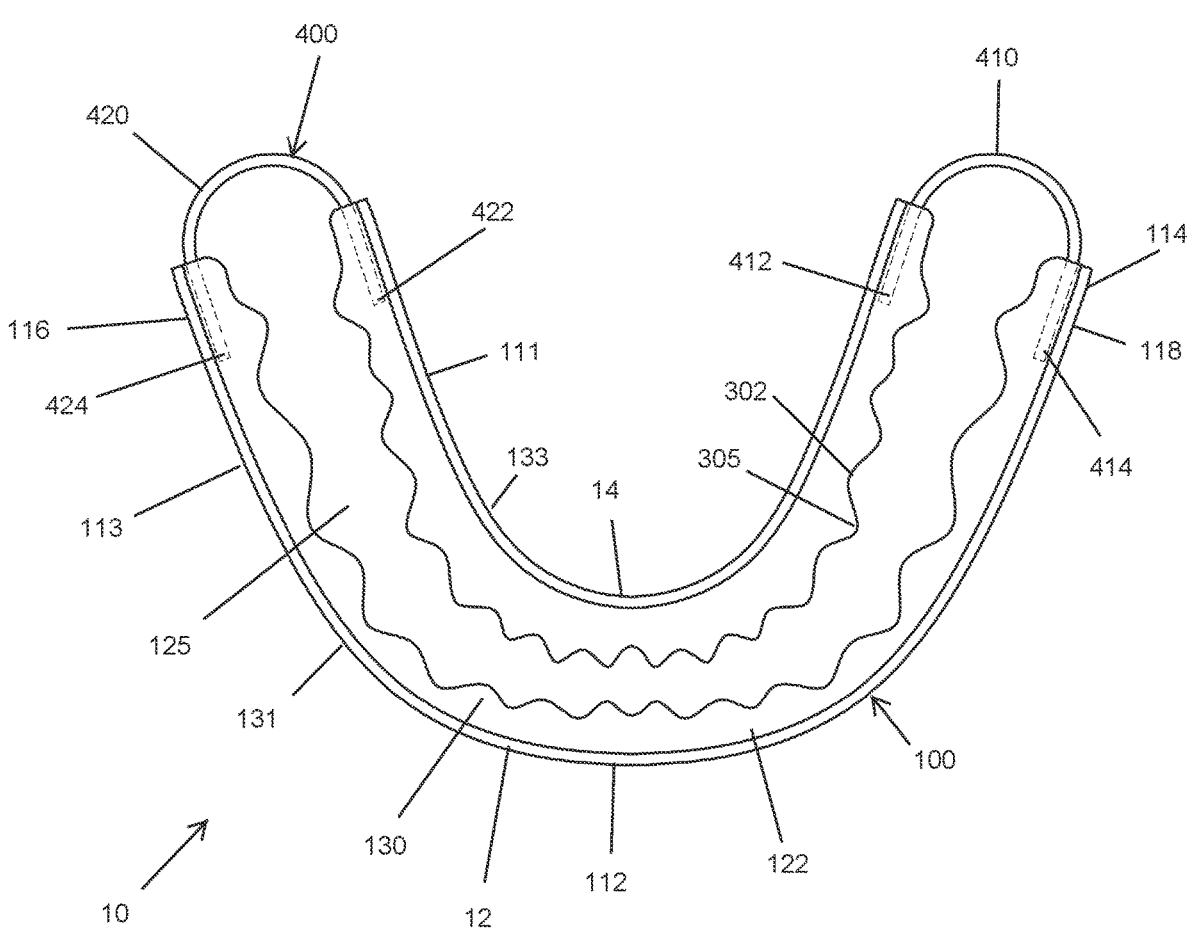
FIG. 12 is a top plan view of the oral appliance of FIG. 11.

The buccal portion 12 and lingual portion 14 of the appliance 10 are connected only by a right side posterior joining portion 126 and a left side posterior joining portion 128 in the illustrated embodiments. In the embodiment shown in FIGS. 4-6, the right side posterior joining portion 126 and left side posterior joining portion 128 are formed from a piece of material which is integrally formed or molded with the buccal portion 12 and lingual portion 14 of the appliance 10. It is desirable however to minimize the thickness of the appliance 10 in the posterior of the appliance, so in some embodiments the buccal portion 12 and lingual portion 14 are joined in the posterior portion 114 of the tray 100 by posterior wires 400, as shown in FIGS. 11 and 12. In such embodiments, a left side posterior wire 410 joins the buccal portion 12 and lingual portion 14 of the appliance in the posterior portion 114 on the left side 118 of the appliance. A proximal end 412 of the left side posterior wire 410 is secured to the buccal portion 12, such as by being inserted into the posterior of the buccal portion 12, while a distal end 414 of the left side posterior wire 410 is secured to the lingual portion 14. Likewise, the right side posterior wire 420 has a proximal end proximal end 422 secured to the posterior of the lingual portion 14, such as by being inserted into the posterior of the lingual portion 14, while a distal end 424 of the left side posterior wire 410 is secured to the lingual portion 14. Metal orthodontic wires can be used to form the posterior wires of the present appliance 10. For example, stainless steel wire, such as 036" (0.9116 mm, 19 gauge) stainless steel wire can be used for the wires.

In the illustrated embodiments, only the posterior portions of the buccal portion 12 and lingual portion 14 of the appliance are joined together. However, in alternative embodiments (not illustrated), one or more additional joining portions 127 can extend between the buccal portion 12 and the lingual portion 14 of the appliance, for example between the right lingual side 132 and right buccal side 136, and between the left lingual side 134 and left buccal side 138. Such additional joining portions can be formed in the same manner as the right side posterior joining portion 126 and left side posterior joining portion 128, such as from a polymer material or wire. Such additional joining portions 127 can provide greater structural stability to the present appliance 10.

Figure 10:
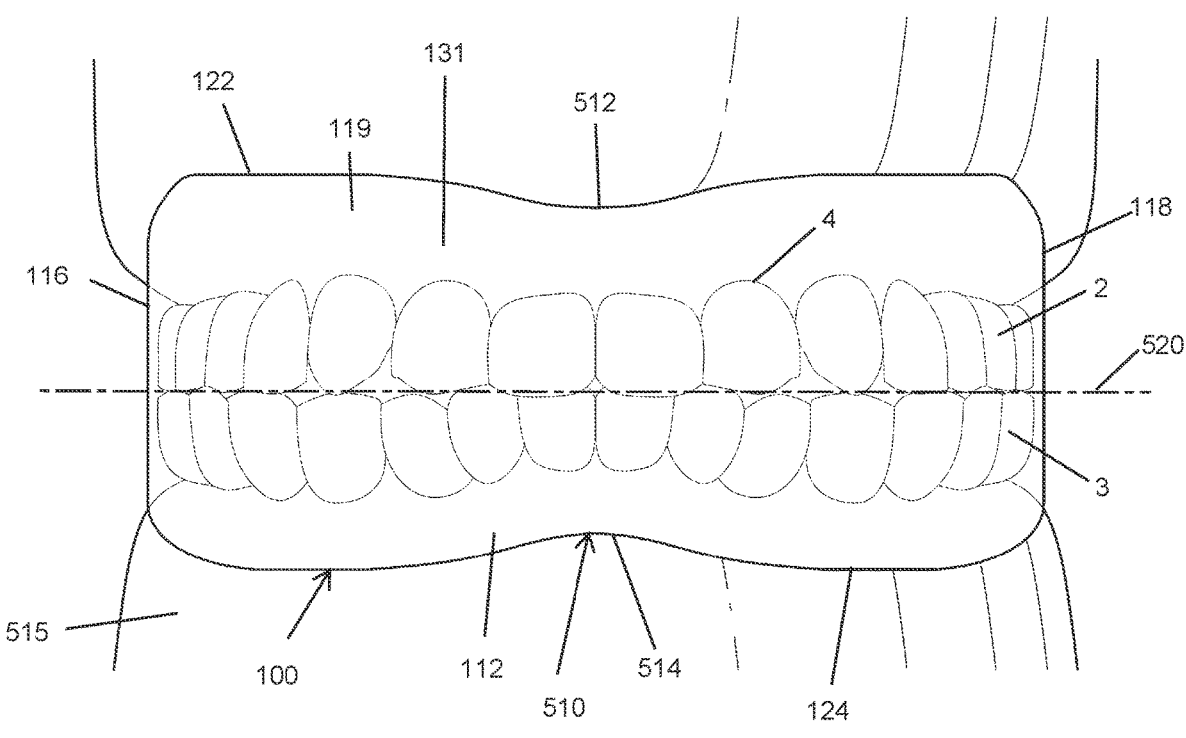
FIG. 10 is a front elevation view of the oral appliance of FIG. 4 mounted on a plaster cast of a subject's teeth.

The present appliance can be produced from a moldable material compatible for oral use, such as a polymer material, in ways known to the art. For example, a digital model or physical impression of a user's teeth can be obtained, and the model or impression can be used to create a model 515 of the user's teeth (as shown in FIG. 10). The model can then be placed into a prepared plastic template for the dental tray 100, and the resulting appliance will be molded to fit the shape of the user's particular dentition. The tray 100 can be formed from a hard polymer material such as acrylic, or can alternatively comprises a soft plastic material which can be thermoplastically shaped to conform to a user's dentition. Such a soft plastic material preferably becomes deformable at a temperature of 212° F. or less, so that the material can be made plastic by being placed in boiling water. Thermoplastic polymers, thermosets, thermoplastic elastomers, and other materials known to the art can be used in this embodiment. When thermoplastic materials are used, they must be capable of retaining their shape when used by a subject, and thus preferably remain solid at least at about 100° F., and preferably remain solid at somewhat higher temperatures, such as at 110° F., 120° F., or higher. In embodiments in which the trays are deformable at a temperature of 212° F. or less, the appliance 10 can be fitted to a user's mouth by placing a softened tray 100 into the user's mouth and having the user bite the material of the appliance while it is still soft, thereby taking on an impression of the user's dentition.

When the present appliance is formed from an impression of a user's teeth (or a model thereof), recesses 500 in the shape of the user's teeth are formed in the upper side 122 and lower side 124 of the dental tray 100, so that maxillary dentition recesses 502 are formed in the upper side 122 and mandibular dentition recesses 504 are formed in the lower side 124. In between such recesses, plastic material extends into the interproximal spaces between teeth (interproximal undercuts), forming interproximal protrusions 505. Such interproximal protrusions 505 are in intimate contact with a user's teeth when the appliance is worn, and such contact assists in retaining the user's jaws in place and prevent the jaws from opening, for example due to friction between the user's teeth and the appliance 10.

Method of Use

Figure 2:
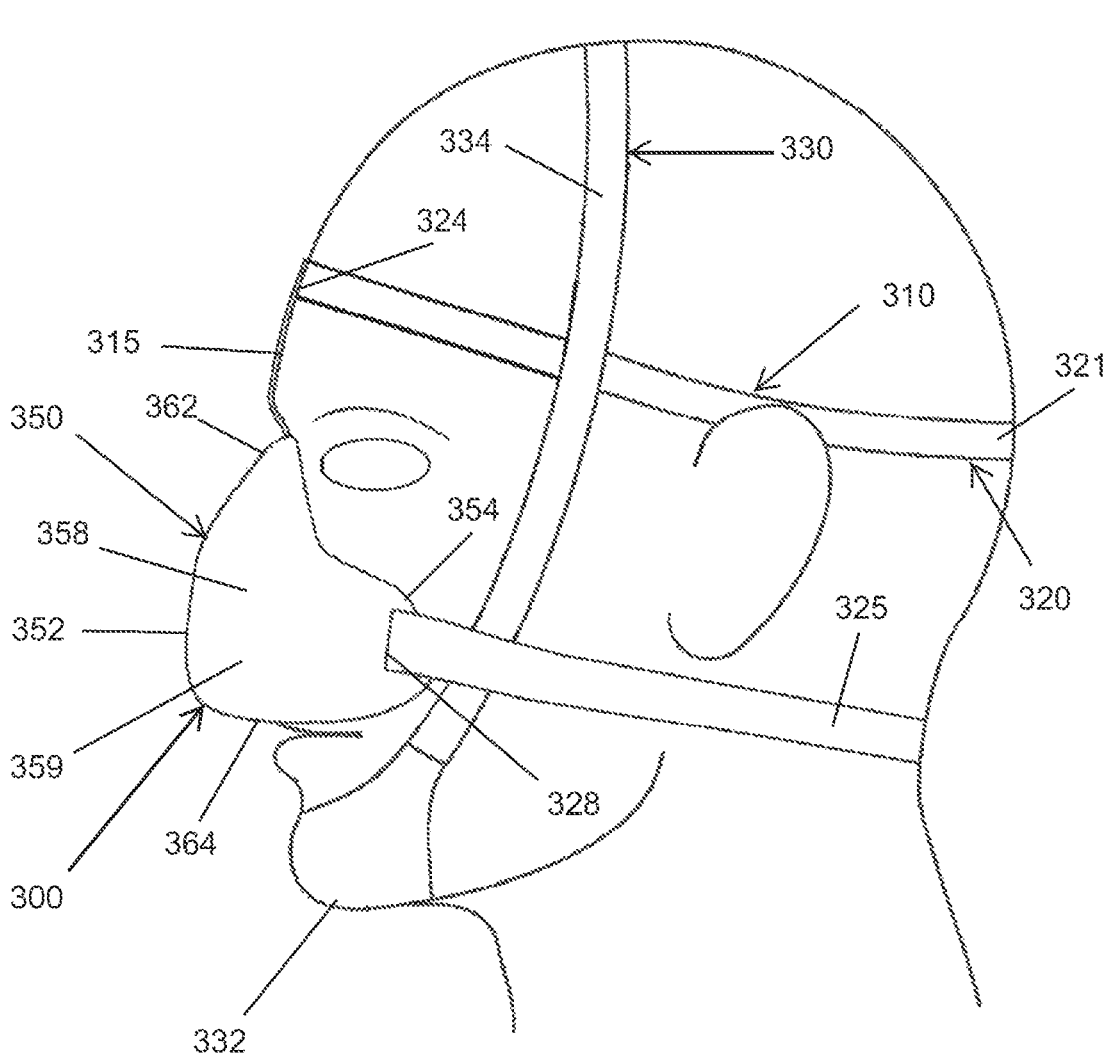
FIG. 2 is a left side elevation view of a subject wearing a CPAP mask and headgear together with the chinstrap of FIG. 1.
Figure 3:
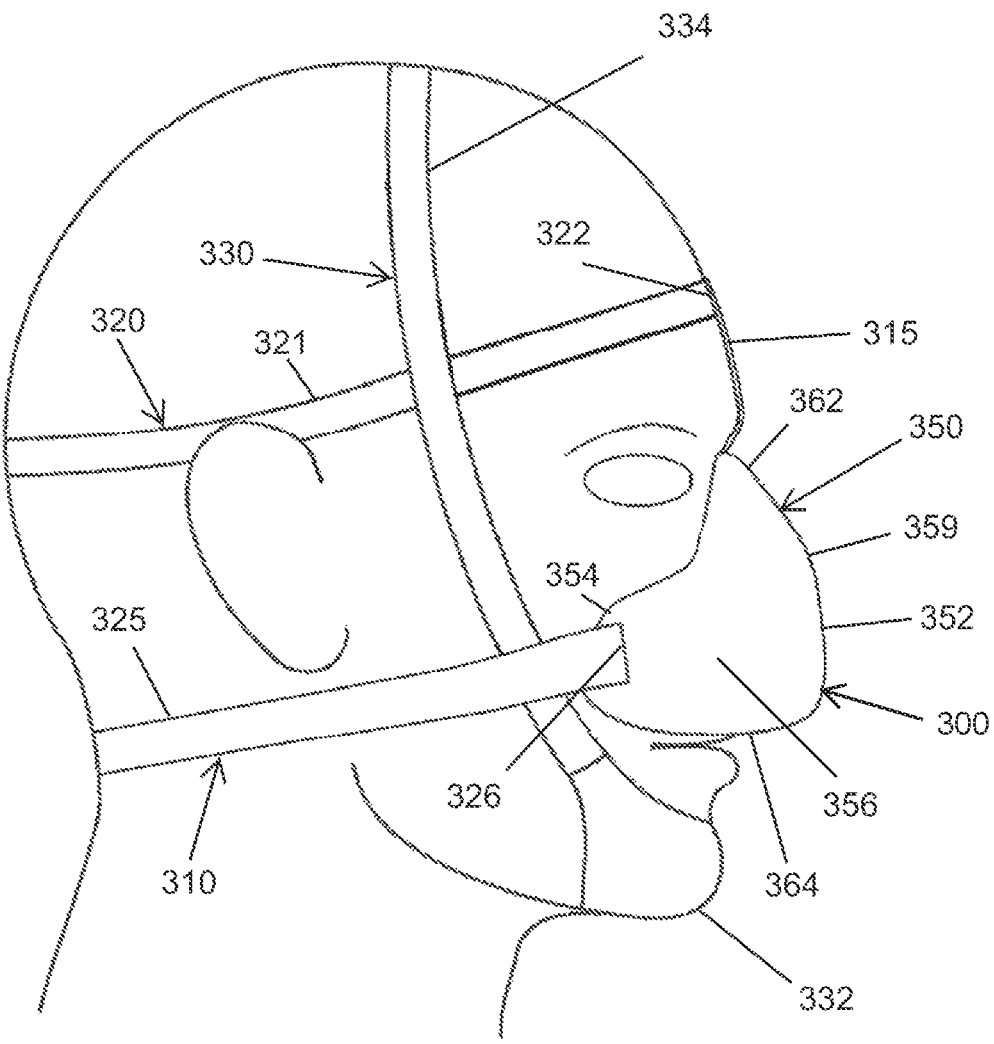
FIG. 3 is a right side elevation view of a subject wearing a CPAP mask and headgear together with the chinstrap of FIG. 1.

The present appliance 10 is used in conjunction with a CPAP system 300 that includes headgear 310 and a nasal mask 350. The nasal mask fits in a sealing manner around the nasal area of a user and includes an anterior portion 352, a posterior portion 354, a right side 356, a left side 358, an inner surface, an outer surface 359, an upper side 362 a lower side 364, as shown in FIGS. 2 and 3. The nasal mask is placed in communication with a source of positive air pressure (not shown) during use.

As shown in FIGS. 1 and 2, the headgear 310 includes one or more lateral straps 320 extending around the head of a user (i.e., extending from an anterior portion around the posterior portion of a user's head) in order to secure the nasal mask 350 to the user's face and head. In the illustrated embodiment, the headgear 310 includes a sagittal strap 315 extending upward from the nasal mask 350 which is attached to an upper lateral strap 321. The sagittal strap 315 is attached a right side end 322 of the upper lateral strap 321, which extends to a left side end 324 around the user's head, with the left side end 324 also being attached to the sagittal strap 315. A lower lateral strap 325 is attached to the sides of the nasal mask 350, with a right side end 326 of the lower lateral strap 325 being attached to the right side 356 of the nasal mask 350. The lower lateral strap 325 extends around the head of the user to a left side end 328 which is attached to the left side 358 of the nasal mask 350. The lateral straps 320 preferably comprise bands of a flexible material for securing the nasal mask 350 to the face of a user.

Prior to the present invention, subjects in some cases needed to wear a chinstrap 330 in order to maintain their mouth in a closed position during use of the CPAP system, as shown in FIG. 1. Such a chinstrap 330 includes a chin retaining portion 332 and a strap portion 334 which extends around the top of a user's head. Maintaining the user's mouth in a closed position during sleep is important, because CPAP systems operate by pumping air under pressure into the airway of a user to prevent collapse of the airway during sleep, which leads to apnea, and if the user's mouth opens then the airway will lose pressure and apnea may not be prevented.

Figure 13:
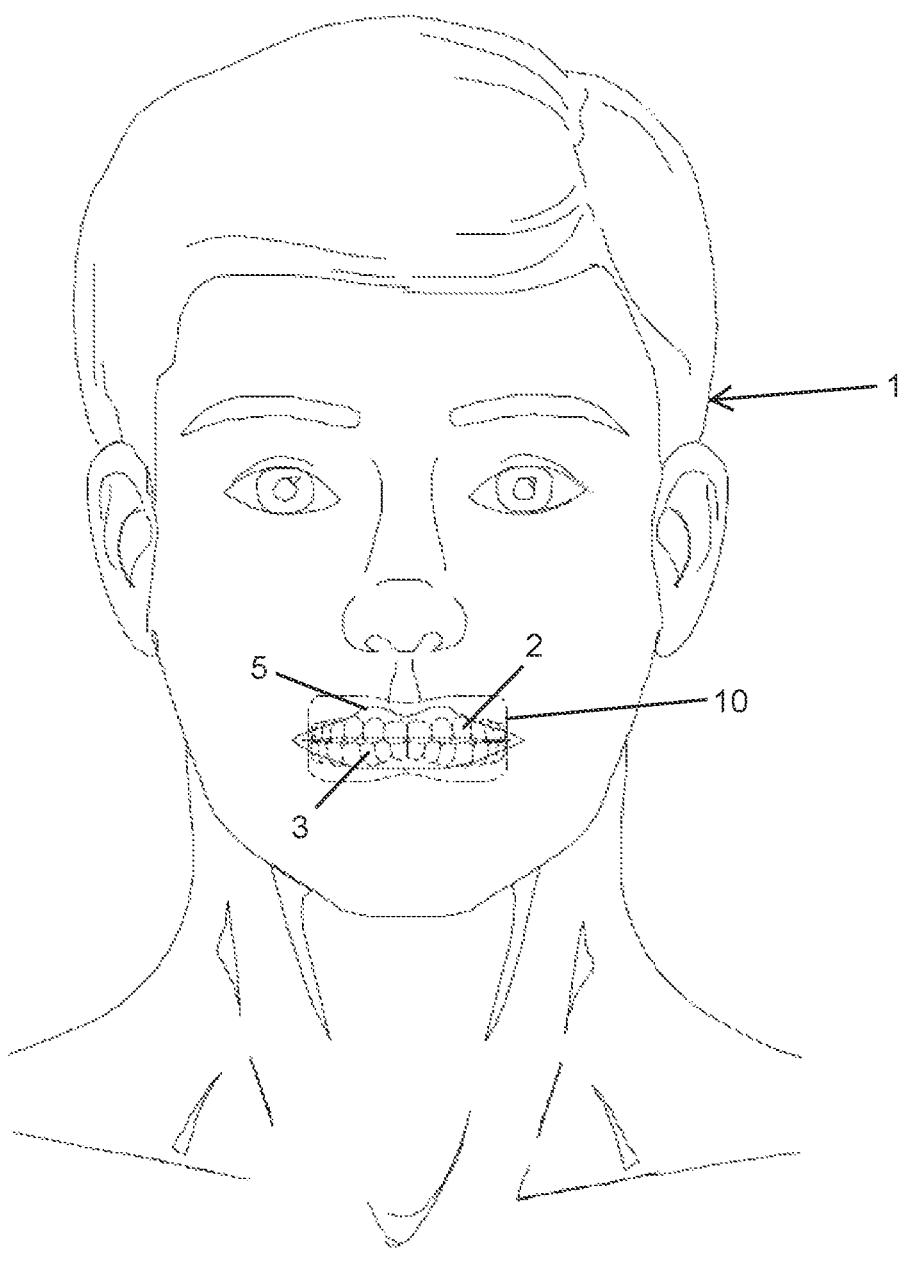
FIG. 13 is a front elevation view of a subject wearing the oral appliance of FIG. 4.

However, by wearing the present appliance 10 during nasal CPAP therapy, the use of a chinstrap 330 is not necessary. In the present method of preventing apnea while using a nasal CPAP mask 350, the present appliance 10 creates an intraoral seal while it is being worn by a user during sleep. As illustrated in FIG. 13, a subject 1 wears the present appliance 10 in the mouth, and the mouth is closed so that the teeth are placed in the appliance's receptacle 130 and the occlusal surfaces of some or all of the maxillary dentition 2 are placed in contact with the occlusal surfaces of some or all of the mandibular dentition 3, in a manner which is the same as or similar to the normal bite of the user while not wearing the present appliance 10. When the user's mouth is closed in this way, the lips 5 naturally come together to close the mouth, and contact between the interior surfaces of the lips 5 and the anterior surface 112 of buccal wall 131 of the appliance which faces the lips forms a seal that substantially or completely prevents leakage of air through the user's mouth. The anterior surface 112 of buccal wall 131 also preferably contacts the inside surface of the cheek to help form the seal.

Although the present invention has been described in considerable detail with reference to certain preferred embodiments, other embodiments are possible. The steps disclosed for the present methods are also not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:

1. An oral appliance for use by a subject while wearing a nasal CPAP mask comprising a dental tray having a lingual side, a buccal side, an anterior portion, a posterior portion, a right side, a left side, an inner surface, an outer surface, an upper side, and a lower side, wherein the dental tray comprises:

a buccal wall having an outer surface on the buccal side of the dental tray, wherein the buccal wall comprises a right buccal side which extends from the anterior portion of the tray to the posterior portion on the right side and a left buccal side which extends from the anterior portion of the tray to the posterior portion on the left side;

a lingual wall having an outer surface on the lingual side of the dental tray, wherein the lingual wall comprises a right lingual side which extends from the anterior portion of the tray to the posterior portion on the right side and a left lingual side which extends from the anterior portion of the tray to the posterior portion on the left side;

a right side joining portion having a proximal end and a distal end, wherein the proximal end is attached to the posterior portion of the lingual wall on the right side and the distal end is attached to the posterior portion of the buccal wall on the right side;

a left side joining portion having a proximal end and a distal end, wherein the proximal end is attached to the posterior portion of the lingual wall on the left side and the distal end is attached to the posterior portion of the buccal wall on the left side;

an occlusal opening extending between the buccal wall and the lingual wall from the anterior portion of the tray to the posterior portion of the tray, wherein the occlusal opening allows the subject's teeth to contact each other when the appliance is worn by the subject;

an upper receptacle portion on the inner surface of the upper side of the tray, wherein the upper receptacle portion comprises a plurality of maxillary dentition recesses for receiving maxillary dentition of the subject, wherein interproximal protrusions extend inwardly from the inner surface of the upper receptacle portion, and wherein each interproximal protrusion is located between adjacent maxillary dentition recesses in order to engage interproximal spaces between the subject's teeth; and a lower receptacle portion on the inner surface of the lower side of the tray, wherein the lower receptacle portion comprises a plurality of mandibular dentition recesses for receiving mandibular dentition of the subject, wherein interproximal protrusions extend inwardly from the inner surface of the lower receptacle portion, and wherein each interproximal protrusion is located between adjacent mandibular dentition recesses in order to engage interproximal spaces between the subject's teeth, wherein contact between the inner surface and interproximal protrusions of the dental tray facilitates maintenance of the subject's jaws in a closed position, thereby allowing the buccal wall to contact the subject's lips and form an intraoral seal, and wherein the occlusal opening forms an open channel extending continuously between the buccal wall and the lingual wall from the anterior portion of the tray to the posterior portion of the tray.

2. The oral appliance of claim 1, wherein the upper side of the buccal wall is configured to extends upwardly beyond the gingival margin of a predetermined tooth by about 4-6 mm.

3. The oral appliance of claim 1, wherein the lower side of the buccal wall is configured to extends downwardly beyond the gingival margin of a predetermined tooth by about 4-6 mm.

4. The oral appliance of claim 1, wherein the upper side of the buccal wall is configured to extends upwardly for a distance which is ⅔ of the distance between the gingival margin of a predetermined tooth and the top of the subject's vestibule.

5. The oral appliance of claim 1, wherein the lower side of the buccal wall is configured to extends downwardly for a distance which is ⅔ of the distance between the gingival margin of a predetermined tooth and the bottom of the subject's vestibule.

6. The oral appliance of claim 1, wherein the upper side and the lower side of the buccal wall extend to at least the alveolar mucosa of the subject.

7. The oral appliance of claim 1, wherein the appliance is formed from a thermoplastic material.

8. The oral appliance of claim 7, wherein the right side joining portion and the left side joining portion are integrally formed with the buccal wall and lingual wall.

9. The oral appliance of claim 1, wherein the right side joining portion and the left side joining portion are each formed from a metal wire having a proximal end and a distal end, wherein the proximal end is attached to the lingual wall and the distal end is attached to the buccal wall.

10. The oral appliance of claim 1, wherein the buccal wall comprises an upper frenum notch.

11. The oral appliance of claim 1, wherein the buccal wall comprises a lower frenum notch.

12. The oral appliance of claim 1, wherein the lingual wall comprises an upper frenum notch or lower frenum notch.

13. A system for treating apnea, comprising the oral appliance of claim 1 and a nasal CPAP mask.

14. A method for treating sleep apnea, comprising the steps of:

wearing the oral appliance of claim 1; and wearing a nasal CPAP mask.

* * * * *